(12) United States Patent
Fitz et al.

(10) Patent No.: US 10,111,782 B2
(45) Date of Patent: Oct. 30, 2018

(54) RESORBABLE LAPAROSCOPICALLY DEPLOYABLE HEMOSTAT

(71) Applicant: Ethicon, Inc., Somerville, NJ (US)

(72) Inventors: Benjamin D. Fitz, Port Murray, NJ (US); Dwayne Looney, Flemington, NJ (US); Thomas Lee Craven, Bridgewater, NJ (US); Clifford Dey, Seabrook, SC (US); Atul Garg, Belle Mead, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 15/450,706

(22) Filed: Mar. 6, 2017

(65) Prior Publication Data

US 2017/0172805 A1 Jun. 22, 2017

Related U.S. Application Data

(62) Division of application No. 13/197,972, filed on Aug. 4, 2011.

(51) Int. Cl.
| | |
|---|---|
| *D04B 1/14* | (2006.01) |
| *A61F 13/00* | (2006.01) |
| *D04H 1/4258* | (2012.01) |
| *D04H 1/46* | (2012.01) |
| *A61L 15/28* | (2006.01) |
| *A61L 15/44* | (2006.01) |
| *A61L 15/64* | (2006.01) |

(52) U.S. Cl.
CPC .. *A61F 13/00012* (2013.01); *A61F 13/00987* (2013.01); *A61L 15/28* (2013.01); *A61L 15/44* (2013.01); *A61L 15/64* (2013.01); *D04B 1/14* (2013.01); *D04H 1/4258* (2013.01); *D04H 1/46* (2013.01); *A61L 2300/418* (2013.01); *A61L 2400/04* (2013.01); *Y10T 442/51* (2015.04)

(58) Field of Classification Search
CPC ........................................................ D04B 1/14
See application file for complete search history.

(56) References Cited

U.S. PATENT DOCUMENTS

| | | | |
|---|---|---|---|
| 3,364,200 A | 1/1968 | Ashton et al. | |
| 3,568,278 A * | 3/1971 | Mattingly | ............. D02G 1/002 |
| | | | 28/171 |
| 3,837,338 A | 9/1974 | Chesky et al. | |
| 3,901,014 A * | 8/1975 | Hiroi | ..................... D02G 1/002 |
| | | | 28/247 |
| 3,937,223 A | 2/1976 | Roth | |

(Continued)

FOREIGN PATENT DOCUMENTS

| | | |
|---|---|---|
| CN | 1298972 | 6/2001 |
| CN | 1310741 | 8/2001 |

(Continued)

OTHER PUBLICATIONS

International Search Report re: PCT/US11/59696 dated May 8, 2012.

(Continued)

*Primary Examiner* — Andrew T Piziali
(74) *Attorney, Agent, or Firm* — David R. Crichton

(57) ABSTRACT

The present invention is directed to a resorbable hemostatic nonwoven felt suitable for use in laparoscopic procedures and to methods for manufacturing said felt.

5 Claims, 1 Drawing Sheet

(56) References Cited

U.S. PATENT DOCUMENTS

| | | | |
|---|---|---|---|
| 4,005,569 A * | 2/1977 | Corbiere | D02G 1/002 28/218 |
| 5,002,551 A | 3/1991 | Linsky et al. | |
| 5,134,229 A | 7/1992 | Saferstein et al. | |
| 5,180,398 A | 1/1993 | Boardman et al. | |
| 5,393,594 A | 2/1995 | Koyfman et al. | |
| 5,503,623 A | 4/1996 | Tilton, Jr. | |
| 5,679,372 A | 10/1997 | Shimuzu et al. | |
| 5,824,335 A | 10/1998 | Dorigatti et al. | |
| 5,914,003 A | 6/1999 | Kosowski et al. | |
| 5,957,939 A | 9/1999 | Heaven et al. | |
| 6,735,835 B2 | 5/2004 | Wong | |
| 7,229,689 B2 | 6/2007 | Qin et al. | |
| 7,252,837 B2 | 8/2007 | Guo et al. | |
| 7,279,177 B2 | 10/2007 | Looney et al. | |
| 7,427,574 B2 | 9/2008 | Allen | |
| 7,645,874 B2 | 1/2010 | Saferstein et al. | |
| 2002/0168911 A1 | 11/2002 | Tonner | |
| 2004/0005350 A1 | 1/2004 | Looney et al. | |
| 2004/0040096 A1 * | 3/2004 | Saferstein | C08B 15/04 8/405 |
| 2004/0101547 A1 | 5/2004 | Pendharkar et al. | |
| 2004/0193088 A1 | 9/2004 | Looney et al. | |
| 2004/0241212 A1 | 12/2004 | Pendharkar et al. | |
| 2004/0243041 A1 | 12/2004 | Qin et al. | |
| 2006/0013863 A1 | 1/2006 | Shalaby et al. | |
| 2006/0084338 A1 | 4/2006 | Shetty et al. | |
| 2006/0258995 A1 | 11/2006 | Pendharkar et al. | |
| 2007/0014862 A1 | 1/2007 | Pameijer et al. | |
| 2007/0036943 A1 | 2/2007 | Hirose et al. | |
| 2007/0066920 A1 | 3/2007 | Hopman et al. | |
| 2007/0160654 A1 | 7/2007 | Ferguson | |
| 2007/0190110 A1 | 8/2007 | Pameijer et al. | |
| 2008/0027365 A1 | 1/2008 | Huey | |
| 2008/0168759 A1 | 7/2008 | Chu et al. | |
| 2009/0018479 A1 | 1/2009 | McCarthy et al. | |
| 2009/0246238 A1 | 10/2009 | Gorman et al. | |
| 2010/0129427 A1 | 5/2010 | Hen et al. | |
| 2011/0070288 A1 | 3/2011 | Andjelic | |

FOREIGN PATENT DOCUMENTS

| | | |
|---|---|---|
| CN | 1450885 | 10/2003 |
| CN | 1694664 | 11/2005 |
| JP | 8-302553 | 11/1996 |
| JP | 2004-174221 | 6/2004 |
| JP | 2004-232160 | 8/2004 |
| JP | 2009-533568 | 9/2009 |

OTHER PUBLICATIONS

International Preliminary Report on Patentability re: PCT/US2011/059696 dated May 14, 2013.

Supplementary European Search Report re: EP11839057 dated Sep. 25, 2015.

\* cited by examiner

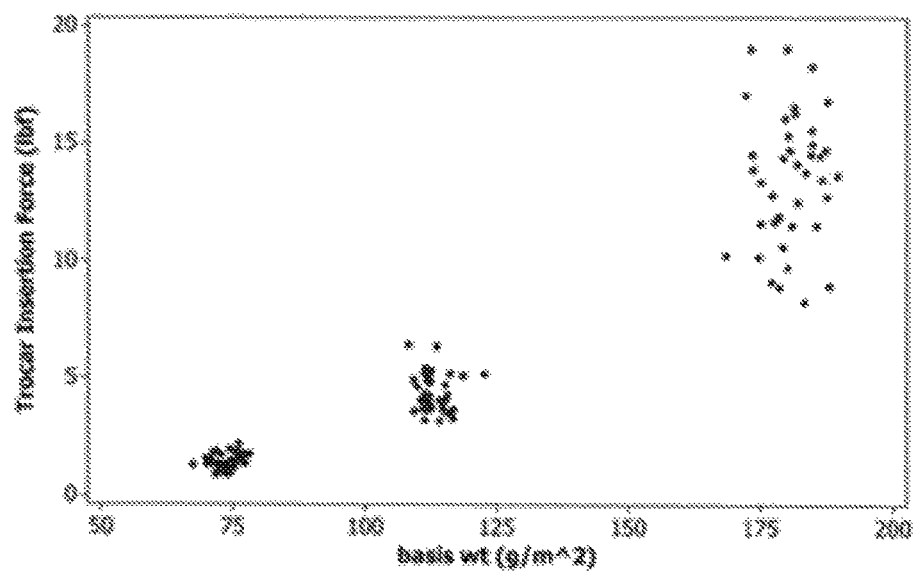

RESORBABLE LAPAROSCOPICALLY DEPLOYABLE HEMOSTAT

RELATED APPLICATION

This application is a Non-Provisional claiming priority from U.S. Provisional Application No. 61/412,120, which was filed on Nov. 10, 2010. The complete disclosures of the aforementioned related U.S. patent applications are hereby incorporated herein by reference for all purposes.

FIELD OF THE INVENTION

The present invention is directed to a resorbable hemostatic nonwoven felt suitable for use in laparoscopic procedures and to methods for manufacturing said felt.

BACKGROUND OF THE INVENTION

The control of bleeding is essential and critical in surgical procedures to minimize blood loss, to reduce post-surgical complications, and to shorten the duration of the surgery in the operating room. Due to its biodegradability and its bactericidal and hemostatic properties, oxidized cellulose, as well as oxidized regenerated cellulose has long been used as a topical hemostatic wound dressing in a variety of surgical procedures, including neurosurgery, abdominal surgery, cardiovascular surgery, thoracic surgery, head and neck surgery, pelvic surgery and skin and subcutaneous tissue procedures. A number of methods forming various types of hemostats based on oxidized cellulose materials are known, made in powder, woven, non-woven, knit, and other forms and combinations thereof. Currently utilized hemostatic wound dressings include knitted or non-woven fabrics comprising oxidized regenerated cellulose (ORC), which is oxidized cellulose with increased homogeneity of the cellulose fiber. Examples of such hemostatic wound dressings commercially available include Surgicel® resorbable hemostat; Surgicel Nu-Knit® resorbable hemostat; and Surgicel® Fibrillar resorbable hemostat; all available from Johnson & Johnson Wound Management Worldwide, a division of Ethicon, Inc., Somerville, N.J., a Johnson & Johnson Company. Other examples of commercial resorbable hemostats containing oxidized cellulose include Oxycel® resorbable cellulose surgical dressing from Becton Dickinson and Company, Morris Plains, N.J.

The commercially available oxidized cellulose hemostats noted above are knitted or non-woven fabrics having a porous structure for providing hemostasis.

U.S. Pat. No. 3,364,200 to Ashton and Moser describes a resorbable, surgical hemostat in the form of pledgets of integrated oxidized cellulose staple fibers. However, there is no suggestion that such pledgets could be used to introduce hemostatic material through a trocar during laparoscopic surgical procedures. The need for very specific properties allowing for hemostatic materials based on cellulose fibers to be introduced into operational space through a trocar or similar device become apparent with the advent and broad spread of the use of the laparoscopic techniques several years after the issuance of the U.S. Pat. No. 3,364,200 in 1968.

Published U.S. Patent Application Publication 2008/0027365 to Huey describes an apparatus for promoting hemostasis utilizing oxidized cellulose in the form of a compressible, shapeable mass that is formed into a sheet for placement on a bleed site and further having a sleeve in a form of a tubular shell dimensioned to receive a limb.

Published U.S. Patent Application Publication 2004/0005350 to Looney et al. discloses hemostatic wound dressings utilizing a fibrous fabric substrate made from carboxylic-oxidized cellulose and containing a porous, polymeric matrix homogeneously distributed through the fabric and made of a biocompatible, water-soluble or water-swellable cellulose polymer, wherein the fabric contains about 3 percent by weight or more of water-soluble oligosaccharides.

Published U.S. Patent Application Publication 2007/0160654 to Ferguson discloses a method for the manufacture of a reinforced gel-forming fabric composite for use as a wound dressing, whereby the gel-forming fiber material in non-woven fabric form is needled into the reinforcing layer from one side so as to penetrate through the reinforcing layer and form a layer of gel-forming fiber material on both sides of the reinforcing layer. The process further involves forming the gel-forming fiber material by non-woven carding, crossfolding of gel-forming fiber, and needling at a needle punch. The teachings of Ferguson are specific to a fibrous material on a supporting layer and to gel-forming materials.

Published U.S. Patent Application Publication 2007/0036943 to Hirose et al. teaches a non-woven absorbent fabric containing crimped fibers, which form a large number of fiber clusters that are distributed all over the first layer, whereby the clusters interconnect to each other to form a network structure in the same first layer. Another fiber layer disposed on a side of the first layer protrudes outwardly between to form a large number of protrusions.

Published U.S. Patent Application Publication 2006/0258995 to Pendharkar et al. teaches a method of making a multilayered fabric comprising a first resorbable nonwoven fabric and one or more a second resorbable woven or knitted fabric. The fabric is specifically multilayered.

Published U.S. Patent Application Publication 2002/0168911 to Tonner discloses an absorbent fleece for use in hospital supplies, comprises a fiber blend of 80-95% viscose and 10% polyester formed into a dry laid, nonwoven web, wherein the web consists of multiple, carded and cross-lapped layers that are consolidated using a needle-punch process, whereby the fleece has a water absorption of at least about 1,000 wt % and an absorbing speed of at least about 20 mm after 10 seconds.

U.S. Pat. No. 7,427,574 to Allen discloses a non-woven washcloth formed from a blend of two different size polyester fibers, the majority of which have a length about half of that of the minority, that are subjected to carding, cross-lapping and needle punching to produce a fabric with inter-engaged fibers. The washcloth has good absorbing and holding properties for a solution containing chlorhexidine gluconate, while also releasing said chlorhexidine gluconate when wiped on skin.

U.S. Pat. No. 7,229,689 to Qin et al. discloses a nonwoven, felt wound dressing formed by carding polysaccharide fibers to produce a web, cross lapping said web to form a thick layer of felt, needle punching the felt to form a needled non-woven structure, and slitting said needled non-woven structure to form individual wound dressings. This invention relates to polysaccharide fibers having water absorption properties characterized by the incorporation within the fibers of at least one substance having anti-microbial properties, and to wound dressings formed from said fibers. The polysaccharide fibers are preferably formed from alginate or alginate containing additional polysaccharide materials to give additional absorbency. The fibers preferably contain a silver compound as an antimicrobial agent.

U.S. Pat. No. 6,735,835 to Wong discloses a method of making a non-woven fabric that includes carding and needle punching. A method of manufacturing a non-woven fabric comprising opening and mixing different input fibers to form a uniform fiber mixture having predetermined proportions of the different input fibers; carding the fiber mixture to form a uniform web of predetermined thickness travelling in a first direction; laying onto the web high tenacity yarns which extend in the first direction and are spaced apart transversely of the first direction; depositing fixed lengths of the web in alternating fashion on a conveyor travelling in a second direction transverse to the first direction to form on the conveyor a mat consisting of overlapping lengths of the web; and needle-punching the mat to form the non-woven fabric.

U.S. Pat. No. 5,824,335 to Dorigatti et al. teaches bioresorbable non-woven fabric materials for use in surgery, said materials constituting threads embedded in a matrix, wherein both the matrix and the threads constitute autocrosslinked hyaluronic acid, with the production of the non-woven surgical fabric that includes carding and needle punching.

U.S. Pat. No. 3,837,338 to Chesky et al. teaches a conformable non-woven bandage comprising a felted cellulosic nonwoven fabric, in which the fibers have substantial freedom of movement relative to each other, is mechanically compacted into a series of undulations, to yield a bandage material that does not decrease in width when elongated by 10% or more.

U.S. Pat. No. 5,503,623 to Tilton teaches instrumentation and method for laparoscopic insertion and application of sheet like surgical material, such as an adhesion barrier, and undertakes to enable the laparoscopic surgeon to utilize large and full size sheets of Interceed™ in abdominal (including pelvic) surgery. In laparoscopy surgery of the abdomen (including pelvis), all instrumentation and all surgical products must be introduced through "ports" consisting of valved sleeves or tubes. To properly and efficiently introduce and apply a large or full size sheet of sheet like material, Tilton provides a method and apparatus of grasping and furling the sheet and then unfurling, releasing and applying it after passage into the patient's abdominal cavity. The instrument consists of an operational grasping and furling portion which is rotated to furl the sheet like material. It is then "backloaded" or drawn into a tubular portion of the instrument, an inserter sheath for passage through the valved "port". Once the sheet like material is in the abdominal cavity it is unfurled. The grasping portion of the instrument provides for proper and easier alignment and then application of the unfurled sheet. Additional flexibility is achieved by an articulation mechanism which allows horizontal movement of the grasping/furling element to produce an angle in the instrument body.

U.S. Pat. No. 5,957,939 to Heaven, discloses a medical device for deploying surgical fabrics at an operative site within a body cavity of a patient. The device includes a deploying member in the form of an elongated inserter shaft with a supporting member in the form of a sheet of plastic attached to a distal end of the shaft. A sheet of surgical fabric is placed on the supporting member and rolled around the inserter shaft. An introducer tube surrounds the rolled-up fabric and supporting member to prevent them from unrolling. The introducer tube may then be inserted into the body cavity and retracted to allow the supporting member to self-unwind the fabric sheet within the body cavity.

SUMMARY OF THE INVENTION

In one embodiment, the present invention is directed to a resorbable hemostatic dressing comprising a single layer of three-dimensionally entangled nonwoven felt that is not separable into distinct layers by hand consisting essentially of oxidized cellulose fibers, wherein the felt has sufficient mechanical strength and flexibility to retain its structural integrity when deployed laparoscopically. The felt can, independently of one another, have a basis weight of from 70 to 200 grams per square meter, a tensile strength of more than 0.89 newtons, a Z-direction tensile strength of more than 0.22 newtons, a tear strength of greater than 0.22 newtons, and water absorption up to about 1000% of its weight. The oxidized regenerated cellulose fibers can have, on average, a diameter from about 5 microns to about 25 microns.

In another embodiment, the inventive dressing having rectangular dimensions of 1 inch×2 inches can have an insertion force for deployment through a laparoscopic trocar that, for a felt having the basis weight of from about 150 to about 200 grams per meter squared, is less than 89 newtons; that, for a felt having the basis weight of from about 100 to about 125 grams per meter squared, is less than 35.6 newtons; or that, for a felt having the basis weight of from about 70 to about 80 grams per meter squared, is less than 13.3 newtons.

In another embodiment, the inventive dressing contains a three-dimensionally entangled felt that consists essentially of strands having a crimp of from about 5 crimps/inch to about 12 crimps/inch and a staple length from about 1½ to about 4¼ inches.

The present invention is also directed to methods for manufacturing the resorbable hemostatic nonwoven dressings described above comprising the steps of providing cellulose yarn having filaments of minimal twist; forming a multi-yarn, single feed circular knitted cellulose fabric having minimal twist; scouring the cellulose fabric; oxidizing the scoured fabric; pliabilizing the oxidized fabric; deknitting the pliabilized fabric to form a continuous strand having a crimp from about 5 crimps/inch to about 12 crimps/inch; cutting the continuous strand to form staples, said staples having length from about 1½ to about 4¼ inches; carding the staples into a carded batt; and needle-punching and three-dimensionally entangling the carded batt to form a single layer non-woven felt. The steps of de-knitting and cutting are preferably performed at low tension or minimal time at high tension. The step of de-knitting is preferably performed without subsequent spooling and followed immediately by cutting. The carded batt can comprise approximately 10 to 17 layers of carded web, more preferably about 12 layers of carded web.

DETAILED DESCRIPTION OF THE INVENTION

According to an embodiment of the present invention, a method of manufacturing of resorbable hemostatic nonwoven felt comprises the steps described below.

The following regenerated cellulose yarns were utilized in preparation of resorbable hemostatic nonwoven felt of the present invention:

150 Denier/42-filament yarn, preferred
100 Denier/90-filament
60 Denier/24-filament Knitting step: A knitted cellulose structure was made using a circular knitting machine. Multiple fiber bundles were brought together into a single tow untwisted. This tow was fed into the knitting machine and a circular knit structure was created. A circular knit is a type of weft knit, in which the material can be continuously unraveled. A 6 inch circular textile thus was generated utilizing a knitting machine set up with a single row of needles in a circular pattern that yielded a de-knittable single jersey knit. Inventors have discovered that avoiding twisting of fibers during knitting further facilitated the later opening and carding step. In the knitting step, a multi-yarn, single feed circular knit was made, representing a continuous "sock" or tube of knit. The multi-yarn single feed was made having none or minimal twist, preferably less than 5/inch of the yarns. The inventors have discovered that presence of substantial twist prior to oxidation resulted in the opening or de-knitting step being substantially more complicated. Oxidation would only increase this level of difficulty based on what we had seen with the non-twisted yarn. The inventors have discovered that the decrease of the tensile properties of the material after oxidation required minimal or no twist in order to successfully perform the further downstream processing including the steps of de-knitting and cutting. The twisted fibers resulted in more complicated de-knitting and higher fiber breakage and increased scrap.

Scouring step, including steam stretch. The purposes of the scouring with steam stretch, as known in the art, are to remove any residual knitting oils and other contaminants on the knit structures. After the scouring step, which is water-based, it is necessary to remove water. In the removal of the water (drying) the knit structure shrinks, which is known for Rayon structures. The steam stretch step is then performed to return the knit structure to near its pre-scouring dimensions. The scouring is performed with hot water with added detergents and subsequent water rinses, as known in the art, followed by the drying step and by the steam stretch consisting of treating the fabric with the steam and simultaneously applying tension, as known in the art.

Oxidation step: The fabric was then oxidized as it is known in the art. Methods of producing highly oxidized tri-carboxylic acid derivatives of cellulose as hemostatic materials, involving two-stage oxidation by successive processing with an iodine-containing compound and nitrogen oxides. A reference is made to the U.S. Pat. No. 7,279,177 and references cited therein, describing hemostatic wound dressings and methods of making same, which is hereby incorporated by reference in its entirety. Oxidized cellulosic materials are typically prepared by preliminary oxidation with metaperiodate or periodic acid to yield periodate-oxidized, dialdehyde cellulose to form the intermediate for forming carboxylic-oxidized cellulose. The dialdehyde cellulose intermediate then is further oxidized by $NO_2$ to yield the carboxylic-oxidized cellulose, which then is used as a hemostatic, anti-microbial and wound-healing agent. Regenerated cellulose and a detailed description of how to make regenerated oxidized cellulose is set forth in U.S. Pat. No. 3,364,200 and U.S. Pat. No. 5,180,398, the contents each of which is hereby incorporated by reference as if set forth in its entirety. As such, teachings concerning regenerated oxidized cellulose and methods of making same are well within the knowledge of one skilled in the art of hemostatic wound dressings. U.S. Pat. No. 3,364,200 discloses the preparation of carboxylic-oxidized cellulose with an oxidizing agent such as dinitrogen tetroxide in a Freon medium. U.S. Pat. No. 5,180,398 discloses the preparation of carboxylic-oxidized cellulose with an oxidizing agent such as nitrogen dioxide in a per-fluorocarbon solvent. After oxidation by either method, the fabric is thoroughly washed with a solvent such as carbon tetrachloride, followed by aqueous solution of 50 percent isopropyl alcohol (IPA), and finally with 99% IPA. Other exemplary descriptions of the oxidation step can be found in U.S. Pat. No. 5,134,229 to Saferstein, et al., describing a process for preparing a neutralized oxidized cellulose product and its method of use, and in U.S. Pat. No. 7,645,874 to Saferstein, et al., describing cellulose oxidation by nitrogen dioxide in a perfluorinated tertiary amine solvent, and in U.S. Pat. No. 5,914,003 to Kosowski, et al., teaching oxidation of cellulose with nitrogen dioxide in a hydrofluoroether solvent, which are hereby incorporated by reference in their entirety.

Pliabilization step. According to an embodiment of the present invention, pliabilizing or stretching a knitted material that has undergone a chemical process of oxidation that has rendered the material stiff was performed. The fabric was pliabilized by techniques known to these skilled in the art. One known method is the method of using rings inside the fabric tube that are held in place by cone shaped pins that are located outside of the tube but interfering with the inner diameter of the rings. The thickness and diameter of the rings vary with the size of the tube. Other methods of pliabilization can be applied, mechanized or manual. The inventors have discovered that innovatively knitting, oxidizing, pliabilizing, and de-knitting of the material resulted in resorbable hemostatic nonwoven felt having advantageous properties for surgical and particularly laparoscopic surgical applications. The inventors have discovered that the pliabilization step resulted in material which was especially suitable for the following step of de-knitting into a continuous strand. After the oxidation step the material looses strength and it was discovered that the loss of strength was 60% or more of tensile strength of after oxidation. For example, the inventors discovered that 12 yarn straight tensile test showed tensile strength of 6.2 lbf for non-oxidized material and tensile strength of only 2.1 lbf for oxidized material. The inventors have discovered that without pliabilization deknitting yields were significantly reduced (less than 40%). It was found that de-knitting the material for cutting always required some amount of pliabilization, performed manually or in a mechanized process. Without the pliabilization the material was constantly breaking and the rate of de-knitting was about 50 to 100 Kg/hr and material had to be de-knitted manually With pliabilization the de-knitting rates were between 400 and 500 Kg/hr.

De-Knitting and Cutting steps: The fabric was then de-knitted into a continuous strand and cut to form fiber staple. De-knitting and cutting was used at low tension or minimal time at high tension, to preserve the crimp for better entanglement and to keep it from breaking in later processes. The tension used was always lower than the strength of the strand, to avoid or minimize the yarn breaks. The tensile strength of ORC yarn was measured using an Instron. In a preferred embodiment the de-knitting tension should be lower than 60 grams-force, as measured by a force gauge. De-knitting was performed without subsequent spooling but with immediately following cutting resulting in preserving crimp. The length of staples was from about 1½ to about 4¼ inches or up to 6 inch. The inventors have tried to use staples which are approximately 1 inch long but the final needlepunched product lacked the structural integrity.

Carding step: the staple yarn was then carded into a carded batt for subsequent needlepunching. In the carding process, staple fibers were input into a machine with rotating cylinders having fine metallic teeth. The staple fiber is "brushed" via the cylinder teeth which act to separate the staple yarn-bundle into individual filaments. The "brushed" filaments (web) were layered on a take-up roller into a batt. Batt was approximately 10 to 17 layers of carded web, typically about 12-layers web forming the carded batt, which was then needlepunched to make a single layer 'felt'.

Needle-punching for 3D entanglement and forming a single layer felt: the fibers formed at the previous step were then needle punched to form the felt of the present invention as follows: The carded batt was fed into the needlepunching process in which a bed of barbed needles penetrated the batt as the batt passes through the machine. The barbed needles pull the batt fibers through each other three-dimensionally entangling the filaments and increasing the structure density. The output of the needlepunch process was the non-woven felt of the present invention.

The inventors have discovered that the material made by the described method and having the following properties was unexpectedly exhibiting the combination of desirable hemostatic properties and structural integrity properties when deployed through a 5 mm diameter laparoscopic trocar. As used herein, the term "nonwoven fabric" includes, but is not limited to, bonded fabrics, formed fabrics, or engineered fabrics, that are manufactured by processes other than, weaving or knitting. More specifically, the term "nonwoven fabric" refers to a porous, textile-like material, usually in flat sheet form, composed primarily or entirely of staple fibers assembled in a web, sheet or batt. The structure of the nonwoven fabric is based on the arrangement of, for example, staple fibers that are typically arranged more or less randomly. The tensile, stress-strain and tactile properties of the nonwoven fabric ordinarily stem from fiber to fiber friction created by entanglement and reinforcement of, for example, staple fibers, and/or from adhesive, chemical or physical bonding. Notwithstanding, the raw materials used to manufacture the nonwoven fabric may be yarns, scrims, netting, or filaments made by processes that include, weaving or knitting.

Example 1. Properties

According to an embodiment of the present invention, the resorbable hemostatic nonwoven felt comprises a single layer of three-dimensionally entangled oxidized regenerated cellulose fibers, wherein the felt has mechanical strength characterized by retention of structural integrity when deployed laparoscopically. The resorbable hemostatic nonwoven felt is further characterized by retention of structural integrity when a rectangular sample having dimensions of 1 inch×2 inches is deployed through a laparoscopic trocar having 5 mm diameter.

The inventors have discovered that the resorbable hemostatic nonwoven felt was resiliently compressible, having sufficient mechanical flexibility, strength, and basis weight for effective use as a hemostat for effective laparoscopic deployment.

The resorbable hemostatic nonwoven felt is further characterized by fast hemostatic activity, with time to hemostasis of approximately 4 to 6 minutes in the porcine linear incision spleen model. The resorbable hemostatic nonwoven felt has a basis weight of from 70 to 200 grams per square meter. The resorbable hemostatic nonwoven felt is further characterized by a tensile strength of more than 0.89 newtons [0.2 LBF] at the same basis weight for the rectangular sample having dimensions of 1 inch×2 inches.

The resorbable hemostatic nonwoven felt is further characterized by a Z-direction tensile strength of more than 0.22 newtons [0.05 LBF]. For comparative purposes, known marketed non-woven fibrillated non-entangled ORC material was attempted to be evaluated for Z-direction tensile strength, and the inventors have found that Z-direction tensile strength was so low that material could not be mounted in tensile testing jig without delaminating.

The resorbable hemostatic nonwoven felt is further characterized by an average tear strength of greater than 0.22 newtons [0.05 LBF].

According to an embodiment of the present invention, the resorbable hemostatic nonwoven felt is made of oxidized regenerated cellulose fibers having diameter from about 5 microns to about 25 microns.

According to an embodiment of the present invention, the resorbable hemostatic nonwoven felt was capable of absorbing about 1000% of its weight in water. The felt tested in a water saturation test was able to absorb about 1000% of its weight in water. The test includes weighing the sample, saturating the sample with water, letting the excess water to drain for a specified time, weighing the sample with water. The felt tested in a water saturation test was able to absorb about 1000% of its weight in water 1000% by weight vs. 400% for knit structures. In comparison marketed nonwoven fibrillated non-entangled ORC material with basis weight of from 200 to 400 grams/meter squared cannot be subjected to this test due to lack of integrity in this test.

DESCRIPTION OF DRAWING

Referring now to FIG. 1, trocar insertion force (dry) for a rectangular sample of the resorbable hemostatic nonwoven felt of the present invention having dimensions of 1 inch×2 inches is shown as a function of the basis weight, as measured by an Instron machine for insertion into a 5 mm diameter trocar, for the felt of the present invention, indicating acceptable insertion forces. It was discovered that the felt retained structural integrity after the insertion, as indicated by absence of tear and approximately same geometric area after deployment.

The insertion force was measured by mounting a laparoscopic dissector in a jig to the top moving-head of an Instron material test machine 5544 with a 100 lb load cell. A 5 mm Ethicon Endosurgery Endopath Xcel trocar was then mounted in the non-moving base. The 1 in×2 in rectangular test article was grasped at a corner in the dissector and inserted through the trocar at 0.5 inch/sec. by the Instron. The compression stress time-course was measured and recorded by the Instron software.

According to an embodiment of the present invention, the resorbable hemostatic nonwoven felt was further characterized by the insertion force for deploying the rectangular sample having dimensions of 1 inch×2 inches through the laparoscopic trocar:
less than 89 newtons [20 LBF] for the felt having the basis weight of from about 150 to about 200 grams per meter squared;
less than 35.6 newtons [8 LBF] for the felt having the basis weight of from about 100 to about 125 grams per meter squared; or
less than 13.3 newtons [3 LBF] for the felt having the basis weight of from about 70 to about 80 grams per meter squared.

Upon exiting from trocar, the felt of this invention was observed to be easier to manipulate and position and the felt was less wrinkled when compared to known knitted hemostats. The felt was exiting from trocar quickly and without additional unfurling effort reverted to the pre-insertion shape, exhibiting resilient compressibility and having sufficient mechanical flexibility, strength, and basis weight for effective use as a hemostat for effective laparoscopic deployment. In comparison marketed non-woven fibrillated non-entangled ORC material with basis weight of from 200 to 400 grams/meter squared was not possible to insert into trocar. When a few layers peeled from the marketed nonwoven fibrillated non-entangled ORC material with basis weight of from 200 to 400 grams/meter squared were inserted into the trocar, the inventors found that such modified sample has lost structural integrity during trocar deployment and exhibited tears and damage.

According to an embodiment of the present invention, the resorbable hemostatic nonwoven felt is made of yarn which is 150 Denier 42-filament yarn, 100 Denier 90-filament yarn, 60 Denier 24-filament yarn, or combinations thereof.

According to an embodiment of the present invention, the resorbable hemostatic nonwoven felt is made of yarns characterized by crimp from about 5/inch to about 12/inch and comprises staples having length from about 1½ to about 4¼ inches.

The inventors have unexpectedly discovered a method of manufacturing and a resulting material which has desirable hemostatic and mechanical properties and is deployable laparoscopically. Specifically, the material has hemostatic properties similar to non-woven oxidized regenerated cellulose materials and mechanical properties enabling laparoscopic deployment similar to knit or woven oxidized regenerated cellulose materials According to an embodiment of the present invention, the resorbable hemostatic nonwoven felt is manufactured by a method comprising the steps of
providing regenerated cellulose yarn having filaments of minimal twist;
forming a multi-yarn, single feed circular knitted cellulose fabric having minimal twist of the yarns;
scouring the cellulose fabric;
oxidizing the fabric;
pliabilizing the fabric;
de-knitting the fabric forming a continuous strand having a crimp from about 5 crimps/inch to about 12 crimps/inch;
cutting the continuous strand to form staples, said staples having length from about 1½ to about 4¼ inches;
carding the staple yarn into a carded batt;
needle-punching and three-dimensionally entangling the carded batt and forming a single layer non-woven felt;
wherein
the steps of de-knitting and cutting are performed at low tension or minimal time at high tension, preserving the crimp;
the step of de-knitting is performed without subsequent spooling but with immediately following step of cutting resulting in preserving crimp;
the carded batt comprises approximately 10 to 17 layers of carded web, preferably about 12 layers of carded web.

The resorbable hemostatic nonwoven felt was further found to have improved properties of being less adherent to the surgical tools and other materials within the surgical operational space, especially when exposed to contact with wet materials and surfaces, and simultaneously provides hemostasis similar to or better than conventional and known cellulose-containing hemostatic wound dressings. Comparative evaluations of the degree to which ORC-based hemostatic agents adhered to surgical instruments and gloves were conducted on the present resorbable hemostatic nonwoven felt in comparison to known marketed non-woven fibrillated non-entangled ORC material. The evaluations were conducted by 21 surgeons (divided between general and trauma surgeons from United States and Europe) with >95% of surgeons finding the inventive resorbable hemostatic nonwoven felt less adhering than known marketed non-woven fibrillated non-entangled ORC material.

In one preferred embodiment, for a 150 denier/42 filament yarn, the diameter of an individual fiber was approximately 18 to 25 microns as measured from SEM image, so the fibers and the yarns used had 150/42 denier per filament (dpf) (~3.6 dpf) down to 100/90 (~1.1 dpf) or approx 5 microns diameter to 25 microns diameter for the filaments.

In the preferred embodiment, the felt is formed of fibers having uniform staple length and or controlled staple length distribution, and lesser amount of fines which are defined as short easily shed fibers fragments. Known ORC-based non-woven materials have higher amount of fines. In comparison marketed non-woven fibrillated non-entangled ORC material with basis weight of from 200 to 400 grams/meter squared had wider distribution and much shorter staples about 0.5-0.6 inch long.

In the preferred embodiment, the felt is a single layer felt and has no layers peelable from each other. In comparison marketed non-woven fibrillated non-entangled ORC material with basis weight of from 200 to 400 grams/meter squared has a plurality of layers that are separable in layers and has a much lower Z-strength. Material was delaminating when attempted to be mounted in the test jig for peeling test.

In the preferred embodiment, the felt has higher entanglement and interlocking of the fibers compared to the known non-woven oxidized regenerated cellulose based hemostatic materials. Mechanical Z-direction entanglement process of needlepunching is utilized. Other types of 3D entanglement can be utilized for instance hydro-entanglement. In comparison marketed non-woven fibrillated non-entangled ORC material with basis weight of from 200 to 400 grams/meter squared has manufacturing method lacking needlepunching process step providing for 3D entanglement.

Example 2. Wet Insertion Through Trocar

For a wet insertion through trocar for a rectangular sample having dimensions of 1 inch×2 inches, it was discovered that the felt retained its structural integrity after the insertion. According to an embodiment of the present invention, the resorbable hemostatic nonwoven felt further has improved properties of being less adherent to the surgical tools and other materials within the surgical operational space, especially when exposed to contact with wet materials and surfaces, and simultaneously provides hemostasis similar to or better than conventional and known cellulose-containing hemostatic wound dressings. Comparative laparoscopic handling evaluations were conducted on the inventive resorbable hemostatic nonwoven felt against marketed fibrillated ORC by 21 surgeons (divided between general and trauma surgeons from United States and Europe) with majority (>80%) favoring laparoscopic handling characteristics of the inventive resorbable hemostatic nonwoven felt.

Example 3. Hemostatic Activity

The Hemostatic activity of the resorbable hemostatic nonwoven felt of the present invention was tested using The Acute Swine Splenic Incision Hemostasis Model. In the Linear Incision Spleen Model 15-mm long×3-mm deep incisions were made on the spleen and the test or control article (A, B, C, or E) was applied to a freshly created wound site followed by an occlusive digital pressure (tamponade). Pressure was initially applied for one minute and was timed using an electronic timer. Following the one-minute initial tamponade, digital pressure was discontinued; the gauze pad on the article was immediately removed. A 30-second hemostasis evaluation period was performed. If free flow bleeding was not observed within 30 seconds, the time to hemostasis was noted, in a minutes: seconds format, and testing was concluded for that article. If free flow bleeding was observed, pressure and gauze were reapplied for additional 30 second tamponade and observation periods until hemostasis was achieved or until the testing period reached ten minutes. At ten minutes, the trial was aborted as a complete failure and recorded as ">10:00" (greater than ten minutes) in the raw data. Hemostasis was determined by the cessation of free flow bleeding in less than ten minutes.

The results of the testing of hemostatic activity are shown in Tables 1-3. Tables 1 and 2 represent two different sets of experiments. Table 3 represents a summary of the result of Table 2. Test articles for Tables 2 and 3:

Control used was gauze which represented negative control.
A—Marketed woven hemostat, single layer
B—Double layer of the article A
C—Single layer of resorbable hemostatic nonwoven felt of the present invention, made from 150 denier circular fiber yarn, oxidized, and made into a non-woven of 100-110 gsm basis weight, packaged in foil and gamma sterilized to a minimum of 30 kGy
E—Double layer of the article C
Approximately 1.5 cm×2.5 cm rectangular pieces of the test articles were used Fast time to hemostasis for the resorbable hemostatic nonwoven felt of the present invention was observed in all tests. Advantageously, time to hemostasis was independent of the number of layers of the resorbable hemostatic nonwoven felt.

TABLE 1

| Number of Layers of resorbable hemostatic nonwoven felt | Hemostasis Time, min Animal 1 | Hemostasis Time, min Animal 2 | Hemostasis Time, min Animal 3 | Hemostasis Time, min Animal 4 |
|---|---|---|---|---|
| 1 | 5:45 | 5:15 | 6:16 | 6:02 |
| 2 | 5:31 | 5:47 | 7:33 | 4:14 |
| 3 | 5:50 | 6:53 | 6:25 | 4:16 |

TABLE 2

| | Time to hemostasis, min | | | | | | | | | | | |
|---|---|---|---|---|---|---|---|---|---|---|---|---|
| Test article | test 1 | test 2 | test 3 | test 4 | test 5 | test 6 | test 7 | test 8 | test 9 | test 10 | test 11 | test 12 |
| Control | >10 | >10 | >10 | >10 | >10 | >10 | >10 | >10 | >10 | >10 | >10 | >10 |
| A | >10 | 8:25 | >10 | >10 | 5:28 | >10 | 9:00 | 8:22 | >10 | >10 | >10 | >10 |
| B | 8:18 | 8:20 | 9:32 | 8:36 | 7:05 | 6:56 | 6:09 | 5:56 | 9:02 | 8:45 | 8:19 | 7:59 |
| C | 5:35 | 4:32 | 5:44 | 5:22 | 9:30 | 5:42 | 9:58 | 5:43 | 8:02 | 7:46 | 5:04 | 6:00 |
| E | 7:25 | 4:40 | 4:13 | 5:04 | 3:43 | 6:02 | 5:52 | 3:46 | 6:44 | 4:36 | 4:08 | 6:22 |

TABLE 3

| Test article | Average Time to hemostasis, min |
|---|---|
| Control | >10 |
| A | >10 |
| B | 8:18 |
| C | 5:43 |
| E | 4:52 |

Example 4. Tear Strength

Tear strength in machine direction cut of the resorbable hemostatic nonwoven felt of the present invention was measured. The tear strength was tested using Instron material testing machine and demonstrated high strength for a non-woven ORC material.

Instron material testing machine was 5500R: TJ 8, having 10 lbs load cell and 90 PSI grips with 1×1.5 inch smooth steel faces. The samples cut in machine direction were provided for tear strength test. Sample preparation included cutting 1 inch in length tear using scissors. This was done to allow clamping of the samples into the Instron grips and to initiate a tear in a controlled direction. The distance between the Instron grips (gauge length) was set at 1 inch. The either side of the cut edge of the sample was loaded on the Instron grips such that 0.5 inch of sample length is inside the grips. The Instron cross head moved at 12 inch/min to propagate the tear along the sample. The test was manually stopped when the tear propagated through the sample. The results of the measurements are presented in Table 4.

TABLE 4

| | Machine direction tear strength | | Cross machine direction | |
|---|---|---|---|---|
| | Strength (lbs) | Extension (in) | Strength (lbs) | Extension (in) |
| LOT A SAMPLE 1 | 0.206 | 6.8 | 0.279 | 2.910 |
| LOT A SAMPLE 2 | 0.244 | 5.33 | 0.116 | 2.640 |
| LOT A SAMPLE 3 | 0.212 | 8.48 | 0.198 | 2.430 |
| Average LOT A | 0.221 | 6.87 | 0.198 | 2.660 |
| LOT B SAMPLE 1 | 0.188 | 2.330 | 0.206 | 2.510 |
| LOT B SAMPLE 2 | 0.224 | 6.010 | 0.218 | 2.760 |
| LOT B SAMPLE 3 | 0.216 | 6.750 | 0.192 | 2.450 |
| Average LOT B | 0.209 | 5.030 | 0.205 | 2.573 |
| LOT C SAMPLE 1 | 0.198 | 6.920 | 0.213 | 6.710 |
| LOT C SAMPLE 2 | 0.232 | 6.740 | 0.098 | 1.220 |
| Average LOT C | 0.215 | 6.83 | 0.143 | 3.926 |
| AVERAGE OF ALL SAMPLES | 0.215 | 6.17 | 0.19 | 2.95 |

Example 5. Tensile Strength and Water Absorbability

Tensile strength was measured in a similar test as described in the Example 4 using an Instron machine and testing the tensile strength in longitudinal direction. All samples tested were 1×2 inch rectangular samples. The results of testing are presented in Table 5.

The water absorbability was tested according to the following procedure. The test includes weighing the sample, saturating the sample with water, letting the excess water to drain for a specified time, weighing the sample with water. The results of testing are presented in Table 5.

The water absorbability for different lots of material from over 850% to over 1000% of weight of water retained as a function of the weight of the resorbable hemostatic nonwoven felt. Comparison with marketed woven and knit ORC based hemostats in the same test indicated lower water absorbability: 360% (basis weight 188.1); 333% (basis weight 253); 136% (basis weight 431).

TABLE 5

| LOT NUMBER | 150/42 H | | | 60/24 H | | | 100/90 H | | |
|---|---|---|---|---|---|---|---|---|---|
| Average Tensile Strength, lbf, Machine Direction | 5.28 | | | 2.62 | | | 3.42 | | |
| Average Tensile Strength, lbf, Cross Machine Direction | 2.53 | | | 1.96 | | | 1.16 | | |
| TEST NUMBER | 1 | 2 | 3 | 1 | 2 | 3 | 1 | 2 | 3 |
| Basis weight, g/m$^2$ | 125.9 | 93.2 | 116.1 | 126.4 | 116.1 | 102.7 | 108.5 | 110.7 | 87.3 |
| % Water absorption | 1049.9 | 1065.1 | 976.7 | 893.2 | 858.5 | 854.4 | 950.0 | 896.1 | 949.4 |

We claim:

1. A method of manufacturing a resorbable hemostatic dressing comprising a single layer of three-dimensionally entangled nonwoven felt that is not separable into distinct layers by hand consisting essentially of oxidized cellulose fibers, wherein the felt has sufficient mechanical strength and flexibility to retain its structural integrity when deployed laparoscopically, said method comprising the steps of:
   a) providing cellulose yarn having filaments of minimal twist;
   b) forming a multi-yarn, single feed circular knitted cellulose fabric having minimal twist;
   c) scouring the cellulose fabric;
   d) oxidizing the scoured fabric;
   e) pliabilizing the oxidized fabric;
   f) de-knitting the pliabilized fabric to form a continuous strand having a crimp from about 5 crimps/inch to about 12 crimps/inch;
   g) cutting the continuous strand to form staples, said staples having length from about 1½ to about 4¼ inches;
   h) carding the staples into a carded batt; and
   i) needle-punching and three-dimensionally entangling the carded batt to form a single layer non-woven felt.

2. The method according to claim 1, wherein the steps of de-knitting and cutting are performed at low tension or minimal time at high tension.

3. The method according to claim 1, wherein the step of de-knitting is performed without subsequent spooling and followed immediately by cutting.

4. The method according to claim 1, wherein the carded batt comprises approximately 10 to 17 layers of carded web.

5. The method according to claim 4, wherein the carded batt comprises about 12 layers of carded web.

* * * * *